(12) United States Patent
Lauff et al.

(10) Patent No.: US 8,693,452 B1
(45) Date of Patent: Apr. 8, 2014

(54) SELF-CHARGING INDIVIDUAL LIFE EVALUATOR NETWORK

(75) Inventors: Sarah M. Lauff, San Diego, CA (US); Ayax D. Ramirez, Chula Vista, CA (US); Russel E. Clement, El Cajon, CA (US); Joel T. Baumbaugh, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 414 days.

(21) Appl. No.: 13/172,497

(22) Filed: Jun. 29, 2011

(51) Int. Cl.
*H04W 4/00* (2009.01)

(52) U.S. Cl.
USPC .......... 370/338; 370/221; 455/41.2; 455/573; 600/301

(58) Field of Classification Search
None
See application file for complete search history.

(56) References Cited

U.S. PATENT DOCUMENTS

| | | | |
|---|---|---|---|
| 6,513,532 B2 | 2/2003 | Mault et al. | |
| 6,694,180 B1 | 2/2004 | Boesen | |
| 6,893,396 B2 | 5/2005 | Schulze et al. | |
| 2003/0065257 A1 | 4/2003 | Mault et al. | |
| 2004/0193068 A1 | 9/2004 | Burton et al. | |
| 2005/0148882 A1 | 7/2005 | Banet et al. | |
| 2005/0216199 A1 | 9/2005 | Banet | |
| 2005/0228300 A1 | 10/2005 | Jaime et al. | |
| 2005/0250995 A1 | 11/2005 | Quy | |
| 2008/0058614 A1* | 3/2008 | Banet et al. | 600/300 |
| 2008/0108481 A1 | 5/2008 | Limma et al. | |
| 2009/0069642 A1* | 3/2009 | Gao et al. | 600/300 |
| 2012/0089370 A1* | 4/2012 | Chebbo et al. | 702/188 |
| 2013/0231574 A1* | 9/2013 | Tran | 600/479 |

\* cited by examiner

*Primary Examiner* — Mohammad Adhami
(74) *Attorney, Agent, or Firm* — SPAWAR Systems Center Pacific; Kyle Eppele; Ryan J. Friedl

(57) ABSTRACT

Physiological conditions of a plurality of individuals are monitored by using signals provided by sensors on each individual. Each individual has, positioned in close proximity to the individual, one or more sensors for sensing a physiological condition of the individual. A control module is capable of communicating with an external communication station and with the sensors. A wireless networked communication link is established between the control module and the external communication station. Indications of the physiological conditions for a plurality of individuals or physiological conditions derived from the physiological sensors, are transmitted on the wireless networked communication link to the external communication station.

10 Claims, 6 Drawing Sheets

SELF-CHARGING INDIVIDUAL LIFE EVALUATOR NETWORK

FEDERALLY-SPONSORED RESEARCH AND DEVELOPMENT

This invention is assigned to the United States Government. Licensing inquiries may be directed to Office of Research and Technical Applications, Space and Naval Warfare Systems Center, Pacific, Code 72120, San Diego, Calif., 92152; telephone 619-553-2778; email: T2@spawar.navy.mil. Reference Navy Case No. 100665.

BACKGROUND

This disclosure relates to biological status monitoring, and more specifically to networked communications of biological status.

SUMMARY

Physiological conditions of a plurality of individuals are monitored through a wireless network. Sensors, positioned in close proximity to an individual, are used for sensing a physiological condition of the individual as a biocondition. A control module is capable of establishing a communication link among sensors, and other control modules and subsequently transmitting information to an external communication station. The control module may be linked with one or more control modules from at least one additional individual, so that a wireless networked communication link is created that includes at least one of a direct communication link between a first control module and the external communication station or a link through a second control module and the external communication station, according to a predetermined shared network communication protocol. The network is used to communicate indications of the biocondition measured by a sensor or a biocondition derived from at least one of the sensors, on the wireless networked communication link, to the external communication station.

DETAILED DESCRIPTION

Currently, biosensors are being used to monitor the welfare of individuals in remote locations during periods of strenuous exercise or dangerous activities. These sensors can track such items as an individual's heart rate, blood pressure, and oxygen levels. Many of today's devices utilize a patient monitoring device that is solely connected to a major monitoring facility, as exemplified by U.S. Pat. Nos. 6,893,396 and 6,694, 180. Both of these patents describe equipment which only allow for wireless communication between the monitoring device and the monitoring facility and while these are useful, they create a very simple network. If there are multiple devices in the same area, wireless traffic will significantly increase making it very difficult to track many individuals at once. This becomes a significant issue in cases where the monitoring is performed during routine activities.

Other uses for biosensor monitoring can include groups for whom health issues are monitored, such as groups with compromised health, infants and young children, and people working in areas of potential environmental hazard such as mines.

Separately, the current battery technology utilized by many monitoring devices restricts the practicality of use in numerous situations. Previous monitoring devices require batteries to be changed at a fairly consistent rate. By using self-charging batteries in sensors that are deployed in a low-power consumption personal area network such as an IEEE 802.15.4 network, it becomes possible to adapt the sensors so that they harvest enough power from ambient vibrations to charge the device.

Accordingly, he disclosed techniques provide an individual life evaluator network with a self-charging mechanism. The communication network may utilize a star or mesh communications topology. The IEEE Standard 802.15.4 protocol is a shared network communication protocol, and is used to relay more than one individual's sensed information to a control module and subsequently to an external communication station for subsequent a data collection and/or monitoring facility.

Figure 1:
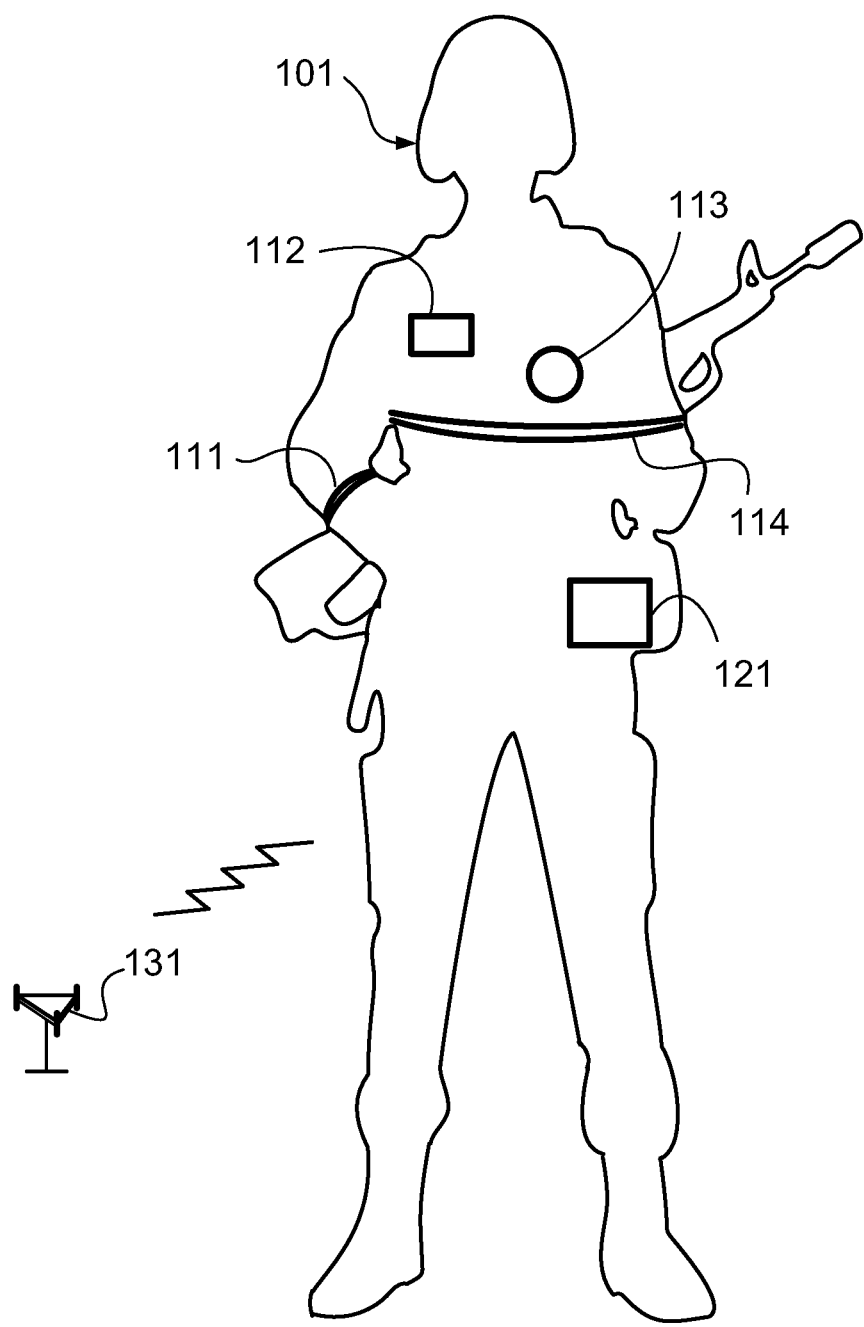
FIG. 1 is a schematic diagram showing an individual wearing biosensors and a control module.

FIG. 1 is a schematic diagram showing an individual 101 wearing biosensors and a communication device. Individual 101 has multiple biosensors 111, 112, 113, and 114 that collect information about the individual's health, and control module 121. By way of non-limiting example, the biosensors can include but are not limited to blood pressure sensor 111, core temperature sensor 112, heart sensor 113, and lung capacity sensor 114. These biosensors 111-114 will check to see if the individual's vital signs are within a predetermined appropriate range either at predetermined time intervals or continuously. Biosensors 111-114 send signals with encrypted messages containing sensed biological data (biodata) to control module 121. Biosensors 111-114 can send the messages containing biodata on an ongoing basis or can send the messages periodically. In one mode of operation if a biosensor detects a significant change in a monitored condition, the sensor will send a message to control module 121. This encrypted message identifies the device or the individual's unique identification number and numerical data about the change in the individual's status. Control module can also monitor biosensors 111-114 to detect a significant change in a reading. Thus the system can function by either biosensors monitoring the readings or the control modules monitoring the person's condition or both.

Control module 121 responds to the messages received from the biosensor and may subsequently send encrypted messages to external communication station 131 concerning the indications of physiological health of the individual 101. These messages from the control module 121 may be sent periodically at predetermined times or when control module 121 detects a set of readings from the biosensors 111-114 indicating a potentially abnormal physiological condition (biocondition) or other potentially abnormal condition. The data may be sent from control module 121 to external communication station 131 via an IP, wireless, or satellite link. In one configuration, the communication link between the control module 121 and the external communication station may use a network connection implementing a framed slotted communication control circuit, such as the 802.11 protocol. Such a circuit is capable of accepting and assigning communication slots according to a predetermined communication protocol. In such a network one station typically provides slot assignments within a network as a master communication station, and other stations in the network communicate according to the protocol using slot assignments that are dictated by the master communication station. Traffic from multiple control modules 121 may be communicated to external communication station. If the external communication uses spread spectrum techniques or otherwise is secure, then it is possible to use the encryption of the communication standard to protect the data that is to be transmitted by the control module 121 to the external communication station 131; otherwise, control module 121 can directly apply encryption to the message received from the sensors 111-114.

The IEEE 802.15.4 standard for wireless personal networks uses Guaranteed Time Slots. This standard is modified under the Life Evaluation Network (LEN) in order to reduce power consumption. The LEN is able to send intermittent signals on a shared multi-user slotted channel network with low latency of signal transmission The LEN has the features of passive network discovery, elimination of polling for possible waiting data, reduced RF spectrum scan for network discovery, the ability to perform transmission time slot requests, custom beacon message content, network existence broadcast messages without frame collisions, network existence broadcast messages with system security and the LEN discovery recurring beacon interval being invariant.

Passive network discovery is achieved because the LEN performs completely passive (no transmissions) network discovery. To do so, the network components respond to a Control Module's (CM) transmission in a prescribed message called Communication Module Advertisement (ConModAd) in accordance with the defined configuration of the IEEE 802.15.4 Standard's MAC and PHY. Network components passively scan a defined subset of the Standard's RF channels to detect ConModAds and choose the best quality signal among multiple CMs. On doing so, the LEN then relays a single encrypted data frame message destined for either a mated end device or a data center that may require retransmissions across LANs and WANs. Thus, management messages, including spontaneous non-compliant messages are ignored in total.

Polling for possible waiting data is eliminated, and instead a procedure allowing passive detection is followed. Network components receive the CMs' ConModAd messages (as above) at network discovery and thereafter according to a battery conservation (wake-up) timing choice. Each ConModAd contains a list of end device identity codes, for devices that have undelivered messages (message waiting) at a CnM. Multiple CMs may hold the same message, to support end device mobility. The LEN relays this information to its mated end device which passively detects its (end device) identity in the list in the ConModAd. On detecting a message waiting for a given end device, that end device transmits one request message to the chosen CM to cause the waiting message content to be transmitted.

RF spectrum scan for network discovery can be achieved without the network devices performing a scan of all available RF channels. A specific subset of channels can be defined. These channels are selected to co-exist with co-located WiFi networks if present. The ConModAd message described above enables passive network discovery with optimal battery conservation.

Transmission time slot requests are achieved by use of carrier sense multiple access (CSMA), implemented as carrier sense multiple access with collision avoidance (CSMA/CA). The CMs with ConModAd message content enable network devices to use the IEEE 802.15.4 Standard's carrier sense multiple access CSMA/CA protocol for medium access rather than time division multiple access (TDMA). Precise message latency management is thus not required, as is the purpose of TDMA time slots. The numerous undesired management messages for time slot acquisition and renewal of existing systems are thus eliminated to support battery-powered and intrinsically low message latency applications.

The custom beacon message content is achieved by allowing network devices to respond to the ConModAd message of the CMs instead of the IEEE 802.15.4 Standard's beacons. The ConModAd messages are ordinary user data messages. Commonly available commercial products need not expect beacon payload content be present. Therefore, no alteration of the Standards-compliant commercial products' firmware is needed. This eliminates the risks and warranty or life cycle support issues arising from altered commercial products used as an element of a larger device.

The IEEE 802.15.4 Standard's beacon transmissions are not used by the LEN. Instead, the CSMA/CA coordinated ConModAd messages are used as described above for low latency, highly reliable data transfer.

Network existence broadcast messages with system security is achieved by layer 2 encryption with a shared key mechanism. The CM devices and overall end to end system design enables end to end encrypted messages to be relayed by the LEN to end devices and the destination data center, using layer 3 encryption, independent of all kinds and sorts of transport networks in the LAN/WAN paths. The LEN supports the CM's ConModAd message content that includes a code to indicate which undisclosed encryption key is required for communicating with the data center affiliated with a given CM. This enables a key unique to each end device mated to the LEN so that compromise of an encryption key does not affect other end devices' security.

The network discovery recurring beacon interval is invariant for a particular network. Each CM's ConModAd message contains a definition of the time until the next (future) ConModAd will be transmitted. Network devices can use the "time until the next ConModAd" to select a power conservation cycle time. The interval may vary from site to site and may vary in time, according to needs such as optimizing battery power consumption strategies, but remains predictable, at least within parameters defined by the network. This reliance on the ConModAd message to provide interoperability among products and suppliers that use different strategies.

The ConModAd has a field that tells the end device when the next ConModAd is being transmitted (i.e., how many seconds after the previous ConModAd). This allows vendors to dynamically adapt their "listening" periods accordingly and thus promotes vendor inter-operability. This reliance on the ConModAd message to indicate a next time of transmission facilitates interoperability among products and suppliers that use different strategies. Traditionally, vendor's set fixed listening periods in their end devices that are optimized their own transmit duty cycles and power management schemes.

In some cases, one or more of the biosensors 111-114 may remain quiescent until activated by control module 121. For example, if there is no specific reason to monitor blood pressure, blood pressure sensor 111 would not activate. Control module 121 can use an external signal and/or data from other sensors 111-114 to determine the activation of particular ones of the biosensors 111-114. This enables either control module 121 or the external signal to provide a signal to cause one or more of the biosensors 111-114 to activate or report a sensed biocondition at the request of control module 121 or an external source. For some types of sensed conditions, the operation of the biosensor consumes significant power or is at least distracting to the wearer (e.g., a blood pressure monitor). Therefore, the ability to cause the biosensors to operate in response to external control allows one or more of the biosensors to remain quiescent except in response to such a request.

Figure 2A:
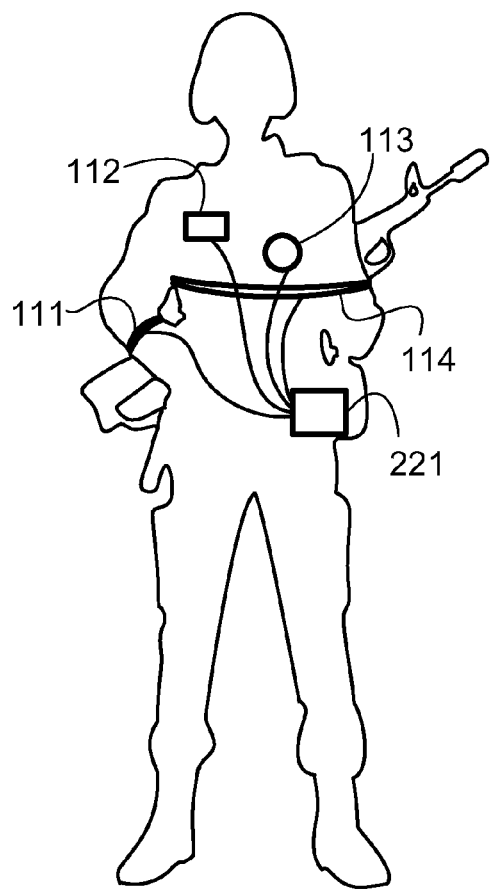
FIGS. 2A and 2B are schematic diagrams showing connection of biosensors to a control module using a wired data bus (FIG. 2A) and wirelessly (FIG. 2B).
Figure 2B:
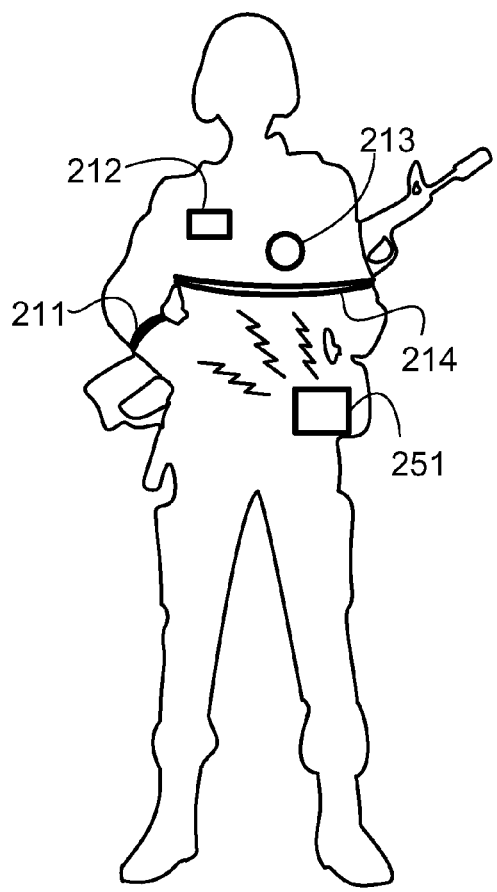

FIGS. 2A and 2B are schematic diagrams showing connection of biosensors to a control module using a wired data bus (FIG. 2A) and wirelessly (FIG. 2B). In FIG. 2A, biosensors 111-114 are connected to control module 221 through a hardwire connection, which can be wires or an optical link such as fiber-optic cabling. This provides advantages in that radio transmissions are avoided for the immediate communication between the biosensors 111-114 and control module 221. This saves energy because encryption and transmission need only occur when communicating the data externally. This allows reading biodata on a frequent basis and transmitting the biodata externally on a less frequent basis. By creating a wired connection between the biosensors and control module 221, confidential data pertaining to an individual's health can be sent to the control module 221 without encryption. This also avoids the need to process data for encryption, which may have an effect on power consumption. A further advantage to hardwire transmission is that it avoids generating a pattern of local transmissions, which could conceivably be detected.

Another way to connect the biosensors to the control module is wirelessly, as depicted in FIG. 2B. Biosensors 211-214 are connected wirelessly using the Life Evaluator Network (LEN) links to control module 251. In order to create this network, biosensors 211-214 act as a Reduced Function Device (RFD). The reason the biosensors are RFDs is because this will force them to only connect with and send their information to a Fully-Functional Device (FFD), which in this case is control module 251. The RFDs can also be set so that information is received by a FFD that is a limited distance away from the individual.

Figure 3:
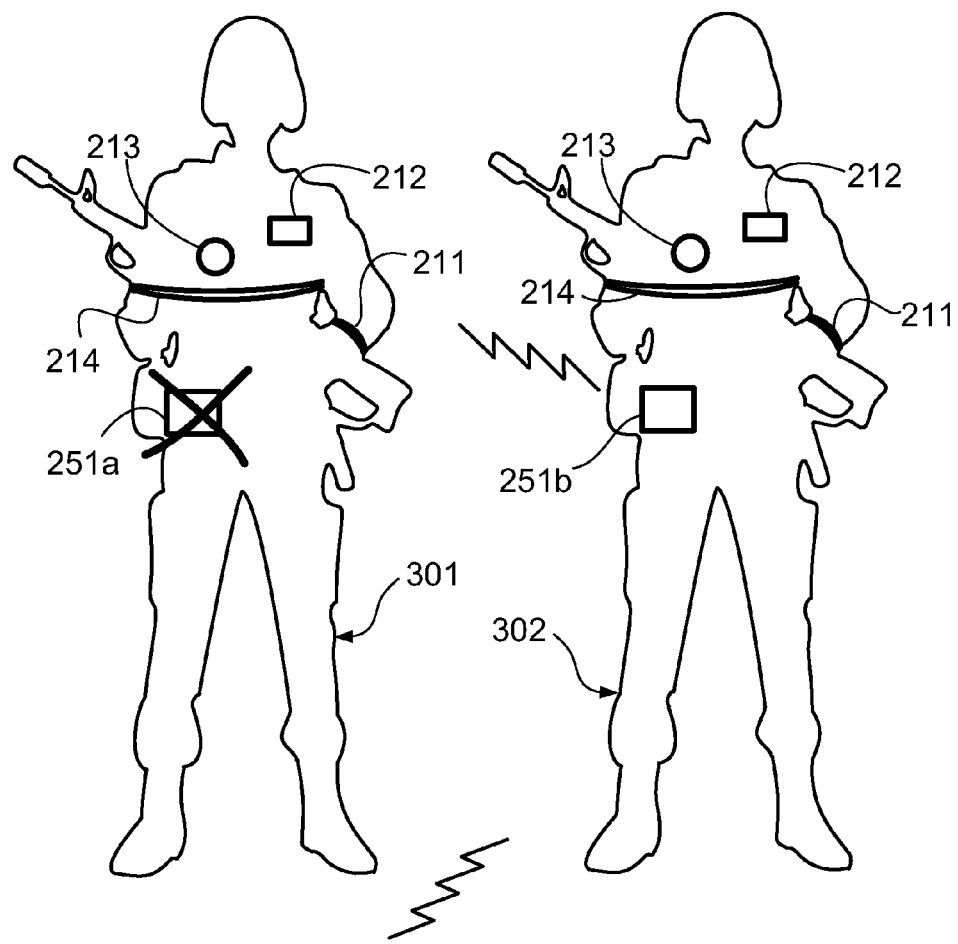
FIG. 3 is a schematic diagram showing a configuration in which sensors are able to communicate wirelessly within a limited distance from the individual.

By creating a wireless connection, the LEN has additional possibilities. One such possibility by using IEEE 802.15.4 devices is that a mesh network can be created in order to prevent single point connectivity failures and to provide network range extension. FIG. 3 is a schematic diagram showing a configuration in which sensors 211-214 are able to communicate wirelessly within a limited distance from the individual.

In FIG. 3, two individuals 301, 302 are depicted, each with biosensors 211-214 and each with control modules 251a and 251b, respectively. If individual 301's control module 251a fails, then individual 301's biosensors 211-214 will not be able to send its data to individual 301's control module 251a. Since biosensors 211-214 are part of an IEEE 802.15.4 mesh network, individual 301's biosensors 211-214 will be able to send their data wirelessly to individual 302's control module 251b as long as they are within range. Individual 302's control module 251b is able to tell that the information it is receiving is from the sensors on individual 301 because a unique identifier (UID) provided as part of the data will signify that the information refers to individual 301. Since biosensors 211-214 are RFDs, the control modules 251a, 251b will "pair" with the other individual's biosensors 211-214 in order to communicate with those biosensors. In this manner, it is possible to create a network where if one individual's control module 251a or 251b ceases to function, the data sent by the biosensors is able to send to another control module 251a or 251b that is within range. This pairing can occur before or after failure of the other individual's control module.

Figure 4:
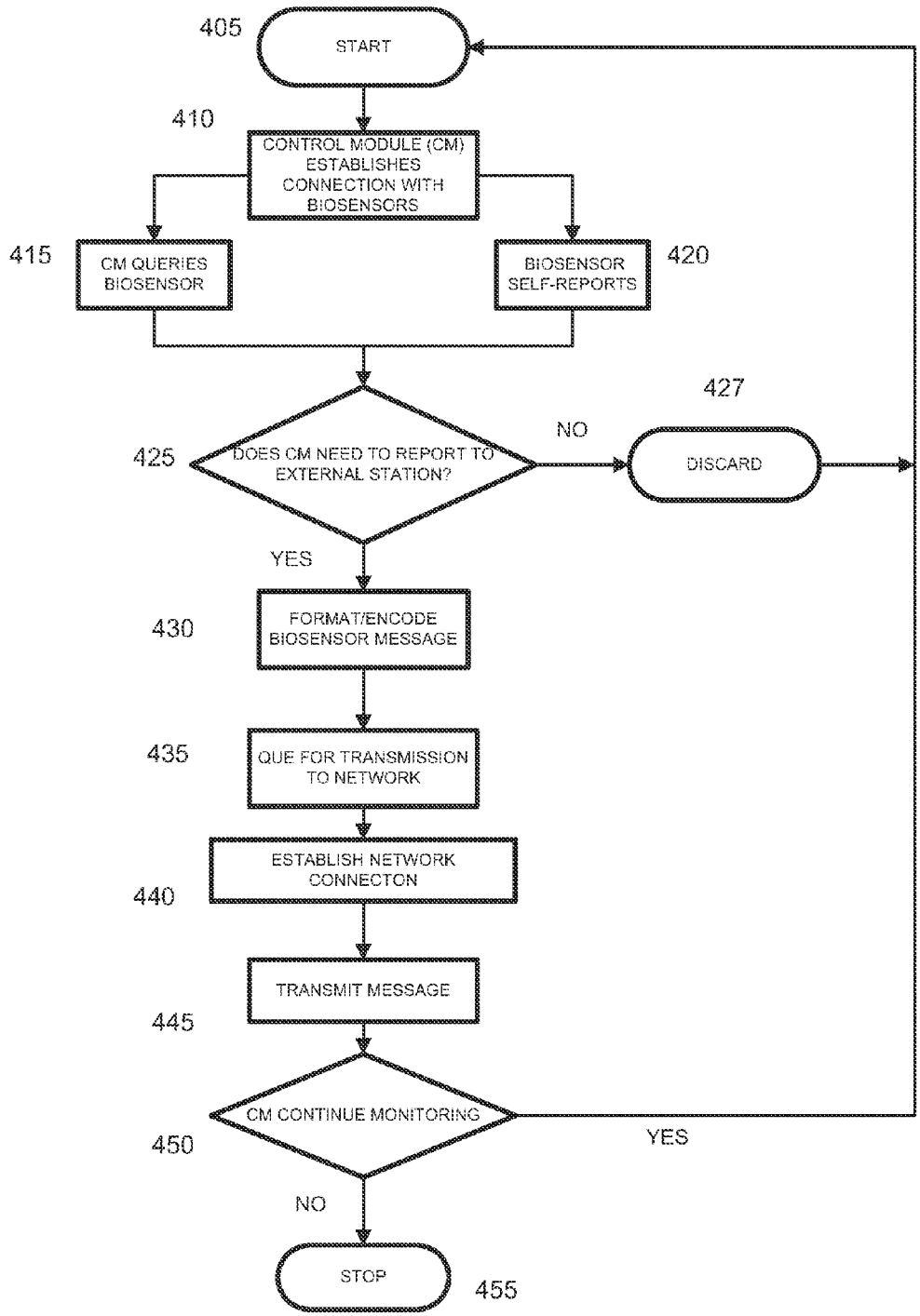
FIG. 4 is a flow diagram showing one implementation of the operation of the biosensor communications system.

FIG. 4 is a flow diagram showing one implementation of the operation of a biosensor communications system. The process is initiated through an integral or external signal (step 405). A control module, such as control module establishes communication with one or more biosensors on an individual (step 410). The control module (either on its own initiative or in response to an external command) queries one or more biosensors for relevant messages concerning one or more physiological conditions of the individual (step 415). Alternatively the control module may receive an unsolicited message from a biosensor, (step 420).

Upon receipt of a message from one or more biosensors, the control module determines (step 425) if a message should be sent to an external communication station. If a determination is made that message should not be reported, the message(s) from the biosensor(s) is discarded (step 427) and the control module reverts to establishing contact with the biosensors. If a determination is made that message should be transmitted to an external communication station then the information received from the biosensors is formatted and encoded (step 430). Since the network may be shared with multiple control modules, the information from the biosenors once formatted and/or encoded are placed in a queue for the subsequent transmission to the external communication network (step 435).

Figure 5:
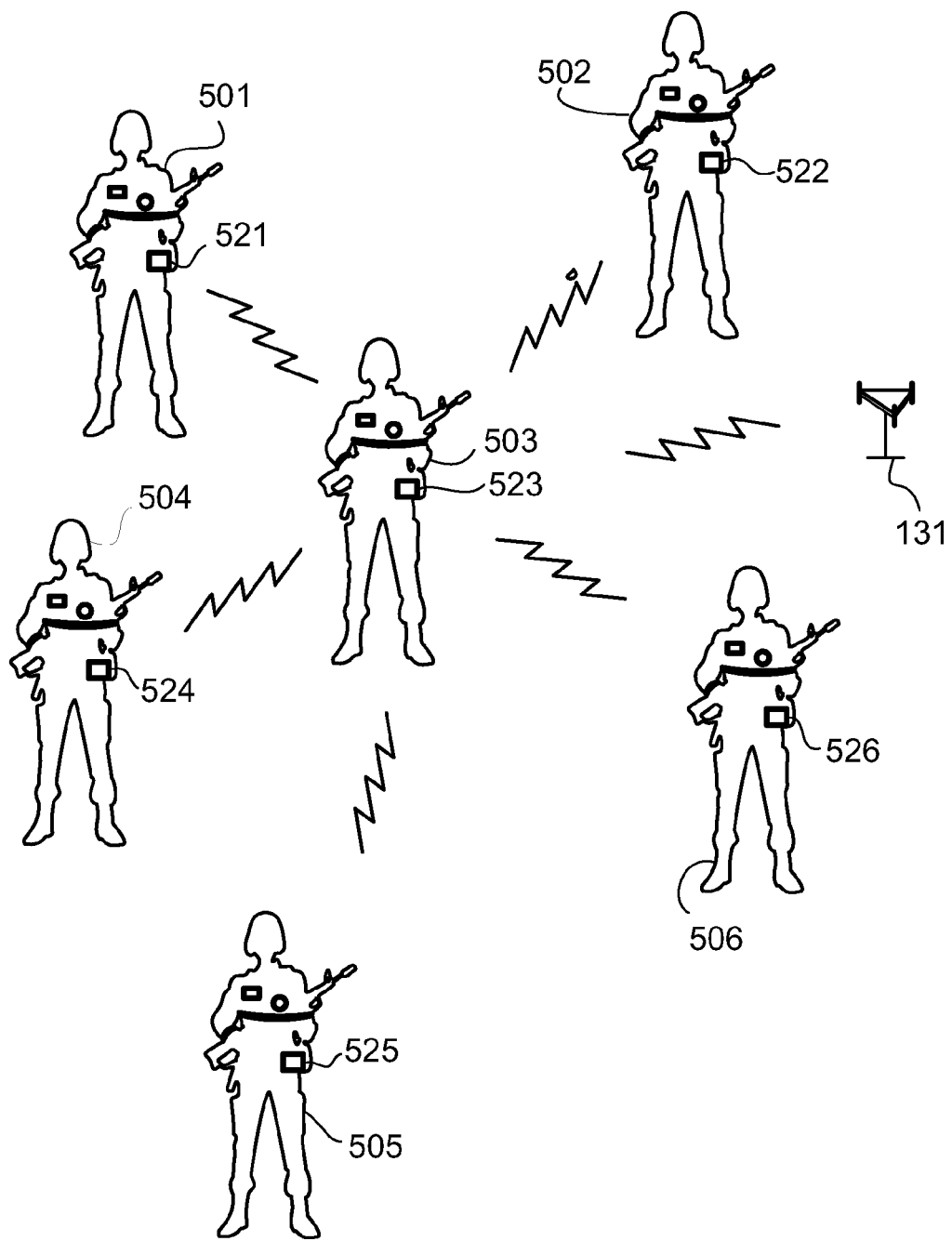
FIG. 5 is a schematic diagram showing a star topography network of biosensors and control modules.

The control module establishes a network connection with the external communication station in order to transmit the now properly formatted and encoded data originally received from one or more biosensors (step 440). Upon establishment of a communication link between a control module and an external communication station the formatted/encoded message is transmitted, (step 445). Once all messages are transmitted between the control module and external communication station the control module must determine whether to return to the condition of connecting with the biosensor or discontinuing further monitoring activity, step 455. Similarly, if another control module requests a network connection, control module receives the request (step 483) and proceeds with communication of the data (steps 451, 453, 471 and 473). FIG. 5 is a schematic diagram showing a star topography network of biosensors and control modules. Depicted are a group of individuals 501-506, equipped with biosensors, such as biosensors 111-114 (FIG. 1), in which control modules 521-526 communicate in a star network. Communication is established between modules carried by individuals within radio range of each other. As depicted, control modules 521, 522, 524, 525 and 526 are able to communicate with control module 523. Additionally, other pairs of control modules carried by individuals, can communicate with each other for example control modules 523 and 524.

With the star topology, each of the control modules normally only connects to external communication station 131 through a single control module 523. To emphasize the fact that only control module 523 can connect to the external communication station, it will be defined as the commanding control module. The commanding control module is the same as all other control modules in the fact that it can receive data from the biosensors and send data to other control modules. There is, however, one major difference—the commanding control module has been given the additional ability to connect to the external communication station and will act as a gateway for the information. Therefore, each of the control modules can only send data to and receive data from the commanding control module 523. The five control modules on the outside (521, 522, 524, 525, and 526) are regular control modules that receive the data from their biosensors 111-114. The individual in the middle 503 therefore provides a link to external communication station 131 for the group. Control module 523 not only gathers information from its associated individual 503 and sends it to external communication station 131, but he also gathers information from the surrounding individuals 501, 502, 504, 505, 506 in order to send the information to the external communication station 131.

The disclosed technology provides an ability of having a control module that self-charges. Most devices today use a wireless protocol such as IEEE Standard 802.11 (WiFi) or Bluetooth that inherently consumes significant battery power, in order to support high data rates. By creating the control modules with the IEEE Standard 802.15.4 Network, the devices will require less power to operate. IEEE 802.15.4 modules, based on current commercial offerings, consume anywhere from 18 to 50 mA of current by the receiver and have a variety of operating voltages. As an example, a typical control module as recommended for use draws 35 mA (0.035 amperes) at 3.3 V. Since this is a very low amount of power, the control module can use a battery that charges by vibrations. An example of such a battery is sold by Infinite Power Solutions of Littleton, Colo. under the name of Thinergy batteries. The vibrational energy of walking/running/crawling would create sufficient energy to power the control module.

The commanding control module 523 in communication with external communication station 131 is not only the communication path for other control modules 521, 522, 524, 525, 526 on other individuals, but is also a control module for the individual wearing it. Therefore, a control module (e.g., commanding control module 523) can collect data from its associated individual 503, while simultaneously sending and receiving data from the other control modules. It has the same functionality as the other control modules 521, 522, 524, 526 with the added ability to connect to the monitoring facility. In one configuration, all control modules 521-526 have this capability of handling data for other control modules and communicating with the external communication station 131.

The external communication station 131 acts as a monitoring facility. Station 131 receives all monitored personnel status information and may be programmed to perform decryption of received data at the facility. If there is a sensor alert or other alert indicated by the monitoring, the external communication station 131 can direct emergency responders to the appropriate individual.

The external communication station 131 is able to send an encrypted message back through the commanding control module 523 to control modules 521-526 based on the sensor/controller UID. The external communication station 131 is able to send a command message that will arm, disarm, and reset a control module 521-526 via connection through the commanding control module 523. Each of control modules 521-526 is able to send and receive data via an IEEE 802.15.4 connection to both the bio-sensors and the commanding control module.

While all of the control modules have the ability to send data via an 802.15.4 LEN connection, the commanding control module 625 has additional abilities. When sending to other control modules 621-626, the commanding control module 625 can only send data via an 802.15.4 link. When sending to the external communication station 131, the commanding control module 626 can send data via an 802.15.4, IP, wireless, or Satellite link.

Figure 6:
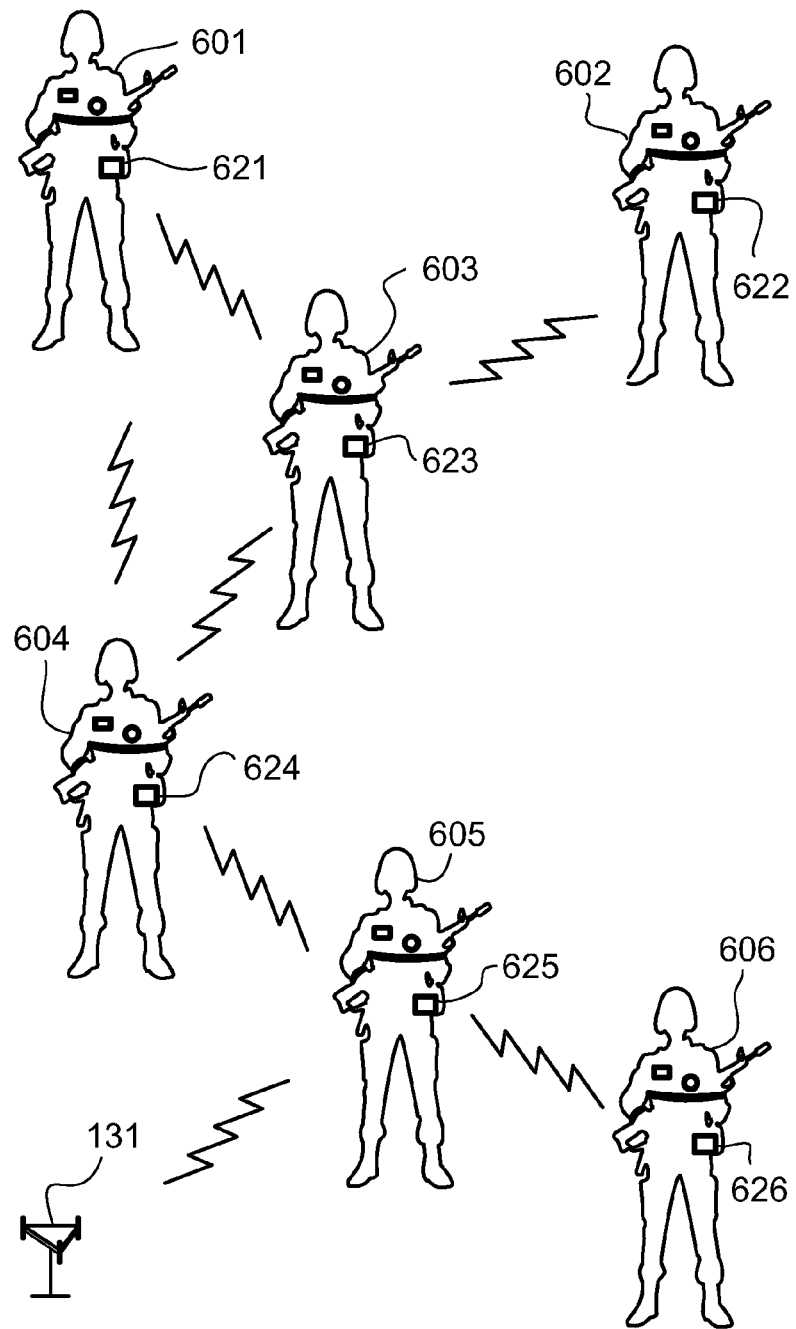
FIG. 6 is a schematic diagram showing a mesh network of biosensors and control modules.

FIG. 6 is a schematic diagram showing a mesh network of biosensors and control modules. Depicted are a group of individuals 601-606, equipped with biosensors, such as biosensors 111-114, in which control modules 621, 622, 623, 624, 625, 626 communicate in a mesh network. Communication is established between modules carried by individuals within radio range of each other. As depicted, control modules 621-626 are able to communicate with each other, either directly or by relay through other control modules. The mesh network differs from the star network in that the routing is established between the nodes (modules 621-626) in an ad-hoc basis, with one or more nodes having the commanding control module ability to communicate directly with the external communication station 131. In FIG. 6, control module 625 has the ability to connect to the external communication station 131 and is therefore a commanding control module.

The control modules 621-626 have the ability to relay communications to the commanding control module 625 through other control modules. FIG. 6 shows this by having data hop from control module 622 to control module 623 to control module 624 and finally to control module 625. Thus, the commanding control module can receive data from 622 via the mesh capabilities through 623 and 624.

In a mesh network, each control module 621-626 is set up to send and receive messages from other control modules. The commanding control module 625 may be an IEEE 802.15.4 device, but is also considered the gateway between the control module 621-626 and the external communication station 131.

The commanding control module 625 in communication with external communication station 131 is not only the communication path for one or more other control modules 621, 622, 624, 626 on other individuals, but is also a control module for the individual wearing it. Therefore, a commanding control module (e.g., module 625) can collect data from its associated individual 605, while simultaneously sending and receiving data from the other control modules. It has the same functionality as the other control modules 621, 622, 624, 626 with the added ability to connect to the external communication station 131. In one configuration, all control modules 621-626 can be commanding control modules and have this capability of handling data for other control modules and communicating with external communication station 131.

As is the case with the star network depicted in FIG. 5, the external communication station 131 receives all monitored personnel status information. Similar as before station 131 may be programmed to be decrypted at the facility. Messages for one of more sensors may be encrypted at station 131, and sent back through the commanding control module 625 to control modules 621-626 based on the sensor/controller UID.

With the mesh topology, the control modules 621-626 are able to communicate with each other, and so when a status message needs to be sent but the control module is out of range of external communication station 131, the information can hop from one control module to another until it is successfully received by a commanding control module. Command messages can be sent back through the chain to update the external communication station.

Alternatively, multiple commanding control modules can be connected to an external communication station 131. Messages may be communicated between external communication station 131 and the commanding control modules, such as 625, via an IP, wireless, or satellite link.

The disclosed techniques include features which include the use of IEEE 802.15.4 devices, the ability to use a star or mesh network for communication with external communication station 131 and ability to maintain power through body movement or vibrations.

IEEE 802.15.4 devices not only have the ability to create a mesh network between control modules, but also a mesh network between the biosensors and control modules. This allows for information to still be sent throughout the network even if an individual's control module fails. A mesh network of biosensors and control modules can implement the IEEE Standard 802.15.4. The IEEE Standard 802.15.4 allows the creation of a mesh network in which, if one control module fails, the information from the biosensors still has the ability to be passed on through another nearby control module. Multiple control modules can be combined into a mobile local network, rather than focusing only on having communication between the control module and the external communication station. One benefit of using the IEEE 802.15.4 devices is the ability to create a mesh network of battery operated nodes. This allows the control modules to connect and securely send their information to the monitoring facility. By having a mesh network, it is also possible to increase the range of external communication station 131. If a control module is out of range of external communication station 131 but in range of another control module, then it can send its data to the other control module so that the data can be passed on to external communication station 131.

This adaptable communication mesh can also be used for other sensors and types of communication such as field communications when other systems fail or encrypted communications are required. In addition, the communication system used by the control module can be used for communications unrelated to biological monitoring. Similarly, the sensed conditions can be indirectly related to biological monitoring, such as the temperature and humidity of the individual's clothing.

The ability to provide power by vibrations is achieved by reducing the power required to monitor and communicate. This makes it possible to adapt the device to charge batteries by vibrations, e.g., walking. This also allows for a long operational lifespan without having to change the batteries. In addition, a network of self-charging batteries can be used in conjunction with chemical and biological sensors.

One alternative is to have the control module collect and analyze the data from all of the biosensors instead of having the biosensors analyze their own data. This would allow for the control module to determine the physiological condition of the individual based on multiple sets of data.

Another alternative is to have the biosensors be able to connect both through wires and wirelessly to the control module. Passing information through cables would minimize the amount of wireless traffic; but if the control module fails, it will still have the ability to send the information wirelessly. Another alternative is to have the batteries be solar powered. This could be implemented in order to augment the power or as a completely different option. An alternative is to also include a GPS device that will help locate a person in distress. When a biosensor detects changes in an individual's status and sends the information to the control module, the control module has the option of including the GPS coordinates of the individual.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. A method comprising the steps of:
providing one or more first sensors for sensing a physiological condition of a first individual as a biocondition, each of the one or more first sensors positioned in close proximity to the first individual;
providing a first control module positioned in close proximity to the first individual and configured to communicate directly with an external communication station and directly with each of the one or more first sensors;
establishing a communication link directly between the first control module and each of the one or more first sensors;
establishing a wireless networked communication link between the first control module and the external communication station;
linking the first control module with a second control module positioned in close proximity to a second individual, the second control module configured to communicate directly with the external communication station and one or more second sensors positioned in close proximity to the second individual and configured to sense a physiological condition of the second individual, wherein the wireless networked communication link comprises at least one of a direct communication link between the first control module and the external communication station and a communication link between the first control module and the external communication station through the second control module;
determining by at least one of the first control module and the second control module a requirement for monitoring at least one biocondition based on an external signal and/or data from other sensors;
providing a signal to cause at least one of the first sensors and the one or more second sensors to activate and report its respective biocondition information, wherein the first sensor and the one or more second sensors remain quiescent except in response to the signal;
communicating a reading from at least one of the one or more first sensors directly to the second control module and from the second control module directly to the external communication station when the first control module fails, wherein the one or more first sensors are paired with the second control module after the first control module fails.

2. The method of claim 1, wherein the wireless networked communication link is a frame slotted wireless communication link, the method further comprising the steps of: using a control module advertisement technique to broadcast signal transmission intervals.

3. The method of claim 1, wherein the wireless networked communication link is a framed slotted wireless communication link, the method further comprising the steps of: using a control module advertisement technique in accordance with the defined configuration of the IEEE 802.15.4 to broadcast signal transmission intervals.

4. The method of claim 1, wherein the step of determining by at least one of the first control module and the second control module a requirement for monitoring at least one biocondition comprises at least one of:
receiving an indication from at least one of the first sensors and the second sensors of a biocondition and determining, externally of such sensor, whether the biocondition indicates a state requiring further monitoring;
receiving an indication from at least one of the first sensors and the second sensors that a biocondition indicates a state requiring monitoring; and receiving a signal through the external communication station requesting monitoring of the biocondition.

5. The method of claim 1, further comprising:
wherein the wireless networked communication link between the first control module and the external communication station is a framed slotted wireless communication link.

6. The method of claim 5,
wherein the wireless networked communication link between the first control module and the external communication station is established in a communication network utilizing a star communications topology.

7. The method of claim 5,
wherein the wireless networked communication link between the first control module and the external communication station is established in a communication network utilizing a mesh communications topology.

8. The method of claim 1, further comprising the steps of:
providing a storage battery and a charging system powered by motion dynamics of the first individual; and
using the storage battery and the charging system to power the first control module.

9. A system comprising:
at least one first sensor, placed in close proximity to a first individual, configured to sense a physiological condition of the first individual;
a first control module configured to establish a communication link directly between the first control module and the at least one first sensor;
a first wireless networked communication circuit providing a first framed slotted wireless communication link directly between the first control module and an external communication station; wherein the first wireless networked communication circuit is configured to selectively communicate indications of the physiological condition sensed by the at least one first sensor using the first frame slotted wireless communication link, to the external communication station;
a first storage battery and a first battery charging circuit configured to generate a charging current in response to body movement of the first individual, the first storage and charging circuit configured to provide power to operate the first control module;

at least one second sensor, placed in close proximity to a second individual, configured to sense a physiological condition of the second individual;
a second control module configured to establish a communication link directly between the second control module and the at least one second sensor and a communication link between the first control module and the external communication station;
a second wireless networked communication circuit providing a second framed slotted wireless communication link directly between the second control module and the external communication station, wherein the second wireless networked communication circuit is configured to selectively communicate indications of the physiological condition sensed by the at least one second sensor using the second frame slotted wireless communication link, to the external communication station;
a second storage battery and a second battery charging circuit configured to generate a charging current in response to body movement of the second individual, the second storage and charging circuit configured to provide power to operate the second control module;
the first and second control module configured to determine a requirement for monitoring at least one biocondition based on an external signal and/or data from other sensors, and configured to provide a signal to cause at least one of the first sensors and the one or more second sensors to activate and report its respective biocondition information, wherein the first sensor and the one or more second sensors remain quiescent except in response to the signal; and
the at least one first sensor configured to communicate directly to the second control module and from the second control module directly to the external communication station when the first control module fails, wherein the one or more first sensors are paired with the second control module after the first control module fails.

10. The system of claim 9, wherein each of the first wireless networked communication circuit and the second wireless networked communication circuit are configured to implement a control module advertisement technique to broadcast signal transmission intervals.

* * * * *